United States Patent
Mi et al.

(10) Patent No.: US 11,142,733 B2
(45) Date of Patent: Oct. 12, 2021

(54) CULTURE FLASK AND CULTURE FLASK ASSEMBLY

(71) Applicant: SCL Biotech Ltd., Apia (WS)

(72) Inventors: Hsin-Wu Mi, New Taipei (TW); Ming-Cheng Lee, New Taipei (TW)

(73) Assignee: SCL BIOTECH LTD., Apia (WS)

( * ) Notice: Subject to any disclaimer, the term of this patent is extended or adjusted under 35 U.S.C. 154(b) by 80 days.

(21) Appl. No.: 16/249,798

(22) Filed: Jan. 16, 2019

(65) Prior Publication Data
US 2020/0123486 A1   Apr. 23, 2020

(30) Foreign Application Priority Data
Oct. 19, 2018 (CN) .......................... 201811221051.1

(51) Int. Cl.
*C12M 1/24* (2006.01)
*C12M 3/00* (2006.01)
*C12M 1/00* (2006.01)

(52) U.S. Cl.
CPC ............ *C12M 23/08* (2013.01); *C12M 23/22* (2013.01); *C12M 23/42* (2013.01)

(58) Field of Classification Search
CPC ...... C12M 45/22; C12M 21/04; C12M 21/14; C12M 23/08; C12M 23/22; C12M 23/42; C12M 23/34; C12M 27/02; C12M 35/04; C12M 29/10; A01N 1/02; A01N 1/0263; A01N 1/0257; A61B 10/0096

(Continued)

(56) References Cited

U.S. PATENT DOCUMENTS 6,210,959 B1 *  4/2001  Lodri ..................... C12M 23/08
                                                                210/296
7,425,440 B2 *  9/2008  Malinge ................ C12M 23/34
                                                                435/243

(Continued)

FOREIGN PATENT DOCUMENTS

CN         206143221 U   *  5/2017
KR       20170074242 A   *  6/2017   ............ C12M 29/20
WO    WO-2016069892 A1   *  5/2016   ............ C12M 29/20

OTHER PUBLICATIONS

CN206143221U Machine English Translation Description (Year: 2017).*

*Primary Examiner* — Michael L Hobbs
*Assistant Examiner* — Lenora A Abel
(74) *Attorney, Agent, or Firm* — Birch, Stewart, Kolasch & Birch, LLP

(57) ABSTRACT

A culture flask has a flask body. The flask body has two translucent planes, one opening end, one recess end and at least one collecting recess. Both translucent planes are located on the opposite ends of the flask body. A collecting recess is formed on the inner surface of the recess end, while the cross sectional area of the recess end gradually decreases toward the bottom of the collecting recess. By forming a collecting recess with decreased cross sectional area, culture cells can be collected inside the bottom after centrifugation, and therefore the user no longer has to transfer the culture cells and culture medium to a centrifuge tube when replacing culture medium. Consumption of suction tube and centrifuge tube can be avoided, the time to replace the culture medium is reduced, and also the risk of contamination when replacing the culture medium is reduced.

7 Claims, 13 Drawing Sheets

(58) Field of Classification Search
USPC ............................ 435/307.1, 304.3, 294.1
See application file for complete search history.

(56) References Cited

U.S. PATENT DOCUMENTS

2005/0194325 A1* 9/2005 Moore ................. B04B 5/0414
210/781
2007/0031963 A1* 2/2007 Chang .................... B01L 3/508
435/304.3

* cited by examiner

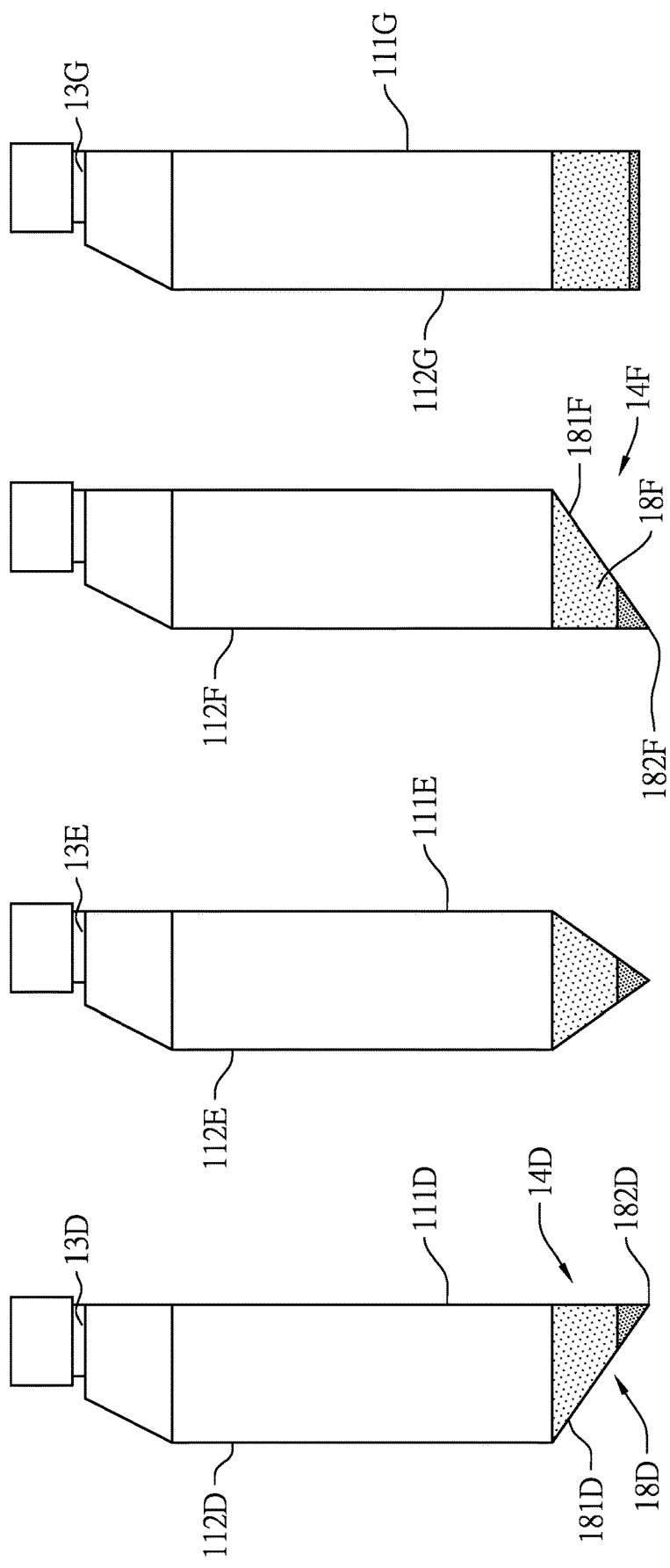

CULTURE FLASK AND CULTURE FLASK ASSEMBLY

CROSS-REFERENCE TO RELATED APPLICATIONS

This application is based upon and claims priority under 35 U.S.C. 119 from China Patent Application No. 201811221051.1 filed on Oct. 19, 2018, which is hereby specifically incorporated herein by this reference thereto.

BACKGROUND OF THE INVENTION

1. Field of the Invention

The present invention relates to a culture flask used in combination with a centrifuge, especially to the culture flask commonly used in a lab in which cells are grown inside and through which cells and culture medium are collected.

2. Description of the Prior Arts

The culture of cells in a lab is commonly done by containing cells and fresh culture medium together inside a culture flask and allowing the cells to grow inside. Chemical composition of the culture medium gradually changes due to the metabolism of the cells, and therefore it is necessary to replace the culture medium inside the culture flask with fresh culture medium on a regular basis to ensure the tissue culture process. To reduce the loss of cells during culture medium replacement, a centrifuge is used for separation between the suspension cells (such as blood cells or trypsinized adhesion cells) that may suspend in the culture medium and the culture medium before removal of the culture medium from the culture flask.

More specifically, the cells and culture medium are contained inside the culture flask for a long time, and the culture of cells requires good ventilation, and therefore a contact area between the culture medium and air needs to be maximized. As a result the culture flask features a flat body, and is disposed horizontally when used for cell culture in order for the culture medium to spread across the flat body and to maximize the contact area between the culture medium and air. Meanwhile, the two flat surfaces on two opposite sides of the flat body can be utilized as translucent planes for users to directly observe cells inside the culture flask using optical instruments.

However, a bottom of the conventional culture flask is generally a flat surface, as a result the cells cannot be brought together in one place after centrifugation, and therefore the cells cannot be separated from the culture medium effectively.

Due to the abovementioned issue, when replacing the culture medium, first the culture medium together with culture cells need to be transferred from the culture flask to a conical bottomed centrifuge tube by using a suction tube, then the centrifuge tube is inserted and fixed inside an adapter whose shape is corresponding to both the inner space of the centrifuge and the outer space of the centrifuge tube, and then the assembled adapter and centrifuge tube is positioned inside the centrifuge to separate cells from culture medium. After centrifuging, cells subside to the conical bottom, the used culture medium on top is then replaced with fresh culture medium, and then the cells along with the fresh culture medium is transferred back to the culture flask to continue the culture of the cells.

However, the shortcoming of aforementioned separation process is that the used suction tube and centrifuge tube need to be disposed of due to the difficulty of cleaning, meanwhile the transfer of container is labor intensive, and the risk of contamination due to improper handling is considerable.

To overcome the shortcomings, the present invention provides a culture flask and a culture flask assembly to mitigate or obviate the aforementioned problems.

SUMMARY OF THE INVENTION

The main objective of the present invention is to provide a culture flask and a culture flask assembly that can be used directly with a centrifuge, and the cells can be collected effectively during the centrifuging process for the ease of use.

The culture flask is configured to contain a culture medium and adapted for centrifugation. The culture flask comprises a flask body. The flask body has two translucent planes, an opening end, a recess end, at least one blocker, and at least one collecting recess. The two translucent planes are located on two opposite sides of the flask body respectively, and the two translucent planes are parallel to each other. At least one of the translucent planes is transparent. The opening end is located on one end of the flask body, a flask opening is formed on the opening end, and the flask opening communicates with an inner space of the flask body. A recess end is located opposite to the opening end on the flask body. An imaginary straight line that passes through both the opening end and the recess end is defined as a centrifuging line. The at least one collecting recess is configured to collect cells in the culture medium. The at least one collecting recess is formed on the recess end and is on an inner surface of the flask body, and an area of the flask body's cross section that is perpendicular to the centrifuging line of the at least one collecting recess is gradually decreased toward a bottom of the collecting recess such that the cells are collected inside the bottom of the at least one collecting recess after centrifugation. The at least one blocker protrudes from the inner surface of the flask body. The at least one blocker is formed on the inner surface of the flask body excluding the two translucent planes, with the blocker extending toward the two translucent planes. Two sides of the at least one blocker is connected to the two translucent planes respectively. The at least one blocker, the inner surface of the flask body, and the two translucent planes form at least one gathering recess. The at least one blocker has a blocking surface facing toward the recess end. The blocking surface inclines toward the recess end, such that an opening of the gathering recess faces toward the recess end to trap and preserve cells moving from the recess end toward the flask opening when the user removes the culture medium by tilting.

The culture flask assembly comprises at least one aforementioned culture flask and an adapter. The adapter has at least one bucket formed on a top of the adapter. A shape of the at least one bucket corresponds to a shape of the at least one culture flask. The at least one culture flask is able to be inserted into the adapter.

The advantage of the present invention is that by having a collecting recess formed inside the flask body and with the collecting recess located opposite to the opening end on the flask body while its cross sectional area gradually decreasing toward its bottom, the culture cells can be collected inside the bottom of the collecting recess after centrifugation, despite the total volume of the culture cells being far less than the volume of the culture medium. The user can easily remove most of the used culture medium by inserting a suction tube into the culture flask and suck out most of the used culture medium from different positions inside the culture flask except from the collecting recess. The user no longer has to worry about the precious culture cells may be removed by accident during the culture medium replacing process.

Meanwhile, by having a collecting recess formed inside the flask body, the user no longer has to transfer the culture cells and culture medium two times when replacing the culture medium, meaning that the user does not have to transfer the culture cells and culture medium from the culture flask to the centrifuge tube by using a suction tube, and then transfer back to the culture flask. As a result, consumption of suction tube and centrifuge tube can be avoided, the time it takes to replace culture medium is reduced, and also the risk of contamination when replacing the culture medium is also reduced.

In addition, the present invention future includes the adapter with its shape being corresponding to the exterior shape of the culture flask. The bucket is formed on top of the adapter, and the shape of the bucket corresponds to the exterior shape of the culture flask. The culture flask can be inserted into the bucket of the adapter with the recess end pointing downward. The exterior shape of the adapter corresponds to the recess inside the centrifuge, and can be inserted into the centrifuge and fixed inside the centrifuge. The centrifugation of the culture flask can be done with normal centrifuge by using the adapter, and the user does not have to purchase a special purpose centrifuge.

Other objectives, advantages and novel features of the invention will become more apparent from the following detailed description when taken in conjunction with the accompanying drawings.

BRIEF DESCRIPTION OF THE DRAWINGS

FIG. 5 is a side view of a fifth embodiment of a culture flask in accordance with the present invention;

FIG. 6 is a side view of a sixth embodiment of a culture flask in accordance with the present invention;

FIG. 7 is a side view of a seventh embodiment of a culture flask in accordance with the present invention;

FIG. 8 is a side view of an eighth embodiment of a culture flask in accordance with the present invention;

DETAILED DESCRIPTION OF THE PREFERRED EMBODIMENTS

Figure 1:
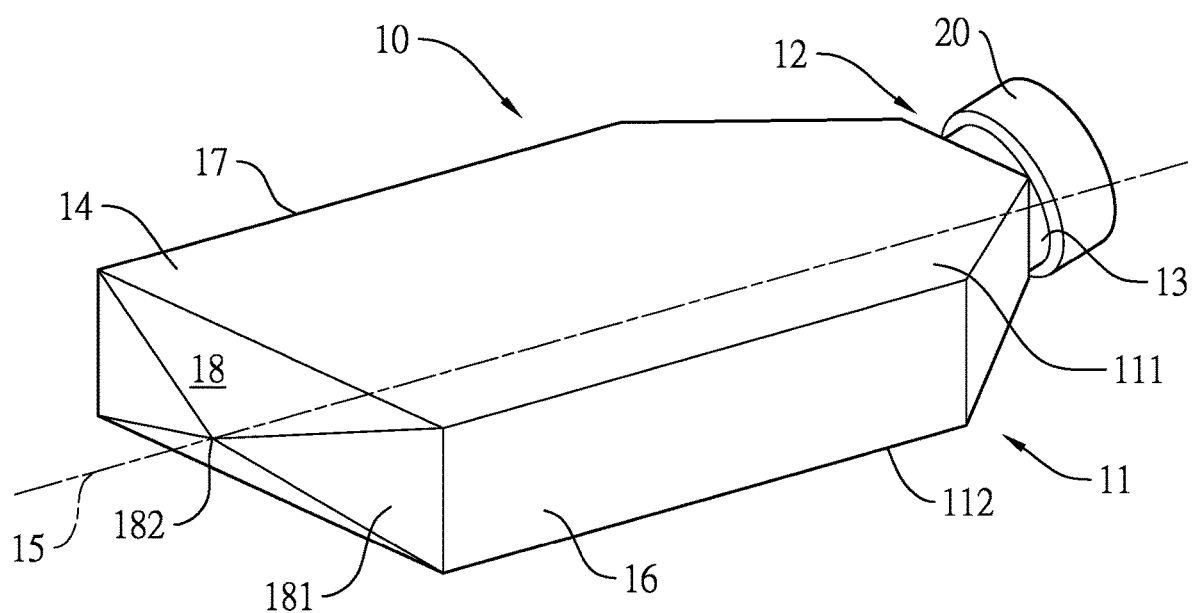
FIG. 1 is a perspective view of a first embodiment of a culture flask in accordance with the present invention.

With reference to FIG. 1, a culture flask in accordance with the present invention comprises a flask body 10 and a flask cap 20.

The flask body 10 has two translucent planes 11. The two translucent planes 11 are located on two opposite sides of the flask body 10 respectively, and the two translucent planes 11 are parallel to each other. In a preferred embodiment, the flask body 10 is flat, and the two translucent planes 11 are located respectively on the two flat sides of the flask body 10. When used for cell culture, the flask body 10 is disposed horizontally with one of the translucent planes 11 facing downward in order for the culture medium to spread across the flat body and to maximize the contact area between the culture medium and air. Using the flat sides as the translucent planes 11 also means that the distance between most of the cells and the translucent planes are roughly same, therefore, minimum focal adjustment is required when the user observes the cells using an optical instrument. The position of the two translucent planes 11 on the flask body 10 is not limited by the abovementioned, which means the two translucent planes can be any two planes on the flat flask body 10 excluding the two flat planes.

In a preferred embodiment, the two translucent planes 11 are respectively an upper translucent plane 111 and a lower translucent plane 112, and both of the two translucent planes 111, 112 are transparent. When used for cell culture, the flask body 10 is disposed horizontally with the lower translucent plane 112 facing downward. The cells attach to the lower translucent plane 112 and grow on it. When the user wants to observe the cells, a microscope is placed under the lower translucent plane 112 while a microscope light source being placed above the upper translucent plane 111. The beam from the microscope light source goes through the two translucent planes 111, 112 and then enters the lens of the microscope for providing sufficient illumination for the cell observation. However, the orientation of the flask body 10 when used for cell culture is not limited. The orientation of the flask body 10 can be flipped, meaning that the flask body 10 is disposed horizontally with the upper translucent plane 111 facing downward.

The flask body 10 has an opening end 12 located on one end of the flask body 10 and a flask opening 13 formed on the opening end 12. An inner space of the flask body 10 communicates with the flask opening 13. A recess end 14 is located opposite to the opening end 12 on the flask body 10. An imaginary straight line passing through both the opening end 12 and the recess end 14 is defined as a centrifuging line 15. In a preferred embodiment, the cross section of the flask body 10 perpendicular to the centrifuging line 15 is a quadrangle. In addition to the two translucent planes 11 corresponding to the two sides of said quadrangle, the other two sides of said quadrangle corresponds to a front side 16 and a rear side 17 respectively on the flask body 10. The front side 16 and the rear side 17 are on the opposite sides of the flask body 10.

In a preferred embodiment, the shape of the cross section of the flask body 10 that is perpendicular to the centrifuging line 15 is not limited to a quadrangle. The shape of said cross section can be a polygon with more than three sides, as long as two sides corresponding to the two translucent planes 11 are included. For example, the shape of said cross section can be a hexagon with the two translucent planes 11 being the two flat sides of the hexagon, and short sides of the flask body 10 corresponding to the inclined sides of the hexagon. In another preferred embodiment, said cross section is in the shape of a racetrack with the two translucent planes 11 being the two flat sides of the racetrack, and the short sides of the flask body 10 corresponding to the semi-circle at each end of the racetrack.

The flask cap 20 is fastened to onto the flask opening 13 by threading. In a preferred embodiment, the flask opening 13 is closer to the upper translucent plane 111 than it is to the lower translucent plane 112, and the flask opening 13 inclines upward toward the upper translucent plane 111 so that the flask body 10 contains more culture medium without spilling when the translucent plane 112 faces downward. However, the flask opening 13 is not limited by the abovementioned; for example, the flask opening 13 can be closer to the lower translucent plane 112 than it is to the upper translucent plane 111, meanwhile, the flask opening 13 inclines upward toward the upper translucent plane 111 so that both the flask opening 13 and flask cap 20 do not protrude from the upper translucent plane 111, and the flask body 10 can be laid flat on a table with either of the translucent planes 11.

The flask opening 13 can be closer to a side more than it is to an opposite side of said side on the flask body 10 excluding the two translucent planes 11. For example, the flask opening 13 can be closer to the front side 16 or to the rear side 17, so that the inclination of the flask body 10 can be reduced when the user wants to empty culture medium inside the flask body 10 by tilting, and therefore it is easier for the user to manipulate. The orientation of the flask opening 13 can be inclined toward a side other than the upper translucent plane 111.

In a preferred embodiment, a collecting recess 18 is formed inside the flask body 10 at the recess end 14, but a number of the collecting recess 18 is not limited to one. A plurality of the collecting recesses 18 can be formed inside the flask body 10 at the recess end 14. In a preferred embodiment, the shape of the collecting recess 18 is a pyramid with a rectangular bottom, and the rectangular bottom of said pyramid faces toward the opening end 12, which means a shape of a bottom of the collecting recess 18 is one point, and a lateral face of the pyramid corresponds to an annular wall 181 of the collecting recess 18, while the pointed top of the pyramid corresponds to a bottom 182 of the collecting recess 18. The shape of collecting recess 18 is not limited to the pyramid with a rectangular bottom, but also can be other kinds of pyramids as long as it is formed by connecting a polygonal shaped cross section of the flask body 10 that is perpendicular to the centrifuging ling 15 and a point. For example, when the cross section of the flask body 10 that is perpendicular to the centrifuging ling 15 is a pentagon, the collecting recess 18 is a pentagonal pyramid. In addition to the abovementioned, the collecting recess 18 can be a cone.

Figure 9:
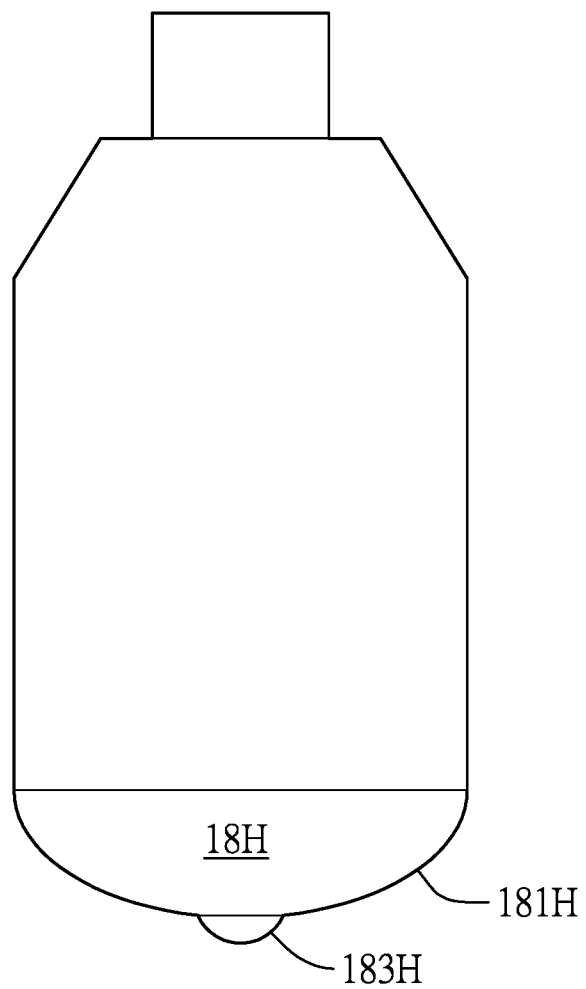
FIG. 9 is a top view of a ninth embodiment of a culture flask in accordance with the present invention.

In a preferred embodiment, the area of the cross section of the collecting recess 18 linearly decreases to a point along the direction of the centrifuging line 15, and therefore the annular wall 18I is comprised by a plurality of planes. However the decrease of the area of the cross section is not limited to be linear, which means the annular wall 181 can be comprised by one or a plurality of curved surfaces. For example the shape of the annular wall 181H of the collecting recess 18H can be a part of one parabolic surface or a part of a sphere as shown in FIG. 9, as long as the area of the cross section of the collecting recess 18 linearly decreases along the direction of the centrifuging line 15, and allowing the cells to slip along an inner surface of the annular wall 181 toward the bottom 182 during centrifugation and finally being collected inside the bottom 182 of the collecting recess 18.

Figure 2:
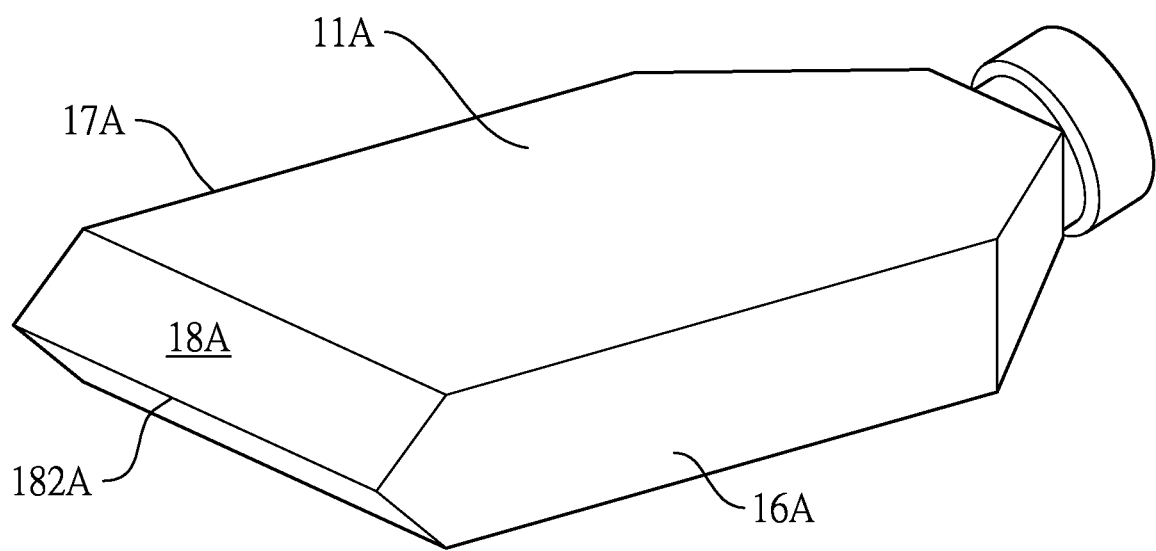
FIG. 2 is a perspective view of a second embodiment of a culture flask in accordance with the present invention.
Figure 4:
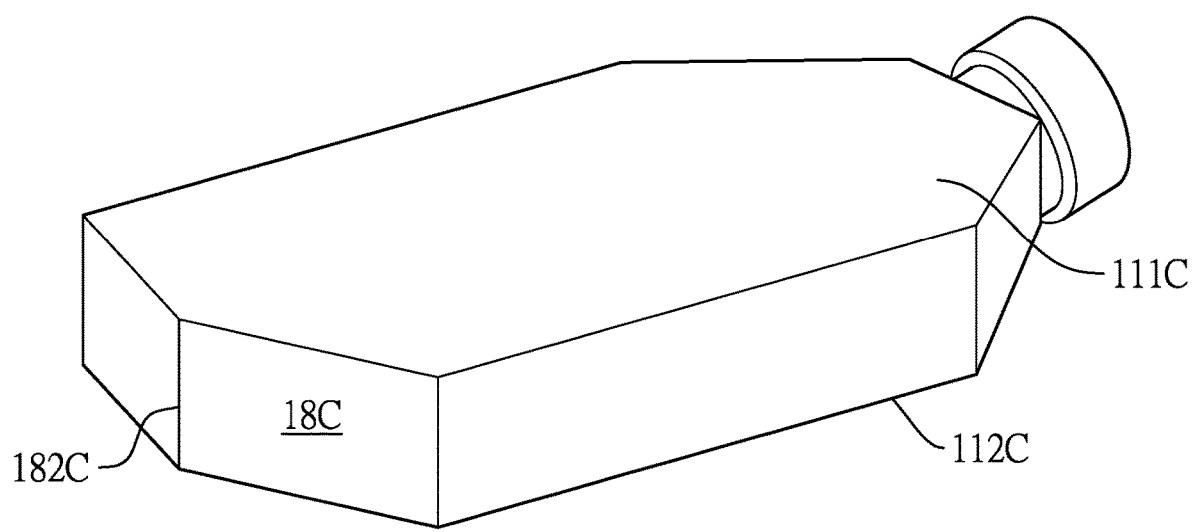
FIG. 4 is a perspective view of a fourth embodiment of a culture flask in accordance with the present invention.

In a preferred embodiment, the area of the cross section of the collecting recess 18 decreases to a point along the direction of the centrifuging line 15, and finally decreases to the bottom 182 in the shape of a point, but the shape of the bottom 182 is not limited to a point. For example, the bottom 182 can also be a straight line or a curve, as long as the area of the cross section of the collecting recess 18 decreases, and the cells can be collected inside the bottom 182. When the bottom 182 of the collecting recess 182 is not in the shape of a point, the collecting recess 18A is not a pyramid due to lack of the apex. For example, the flask body 10A has a front side 16A and a rear side 17A parallel to each other and both sides are perpendicular to the two translucent planes 11A, and meanwhile, the bottom 182A of the collecting recess 18A is in the shape of a straight line which is perpendicular to and connects the front side 16A and rear side 17A, and the shape of the collecting recess 18A is a long prism as shown in FIG. 2. In another preferred embodiment, when the bottom 182C is in the shape of a straight line that is perpendicular to and connects the upper translucent plane 111C and the lower translucent plane 112C, the shape of the collecting recess 18C is a short prism as shown in FIG. 4.

In a preferred embodiment, the distance between the bottom 182 of the collecting recess 18 and the upper translucent plane 111 of the flask body 10 and the distance between the bottom 18 and the lower translucent plane 112 are equal, but the position of the bottom 182 is not limited by the abovementioned. For example, in between the two translucent planes 11, the position of the bottom 182 can be closer to the upper translucent plane 111 than the lower translucent plane 112, or the bottom 182 can be one edge of the upper translucent plane 111 or one edge of the lower translucent plane 112. When the bottom 182 is one edge of the upper translucent plane 111 or the lower translucent plane 112, part of the upper translucent plane 111 or part of the lower translucent plane 112 which is in proximity to the recess end 14 forms one lateral face of the annular wall 181.

In a preferred embodiment, the distance between the bottom 182 of the recess end 18 and the front side 16 of the flask body 10 and the distance between the bottom 182 and the rear side 17 are equal, but the position of the bottom 182 is not limited by the abovementioned. For example, in between the front side 16 and the rear side 17, the position of the bottom 182 can be closer to one side than the other side, or the bottom 182 can be an edge of the front side 16 or the rear side 17. When the bottom 182 is one edge of the front side 16 or one edge of the rear side 17, part of the front side 16 or part of the rear side 17 which is closer to the recess end 14 forms one lateral face of the annular wall 181 of the collecting recess 18.

With reference to FIG. 2, a second embodiment in accordance with the present invention is substantially similar to the first embodiment mentioned above, but the difference is that the collecting recess 18A is an elongated slot. To be more specific, the bottom 182A of the collecting recess 18A is in the shape of a straight line which is perpendicular to and connects the front side 16A and rear side 17A, and the shape of the collecting recess 18A is therefore a long prism.

Figure 3:
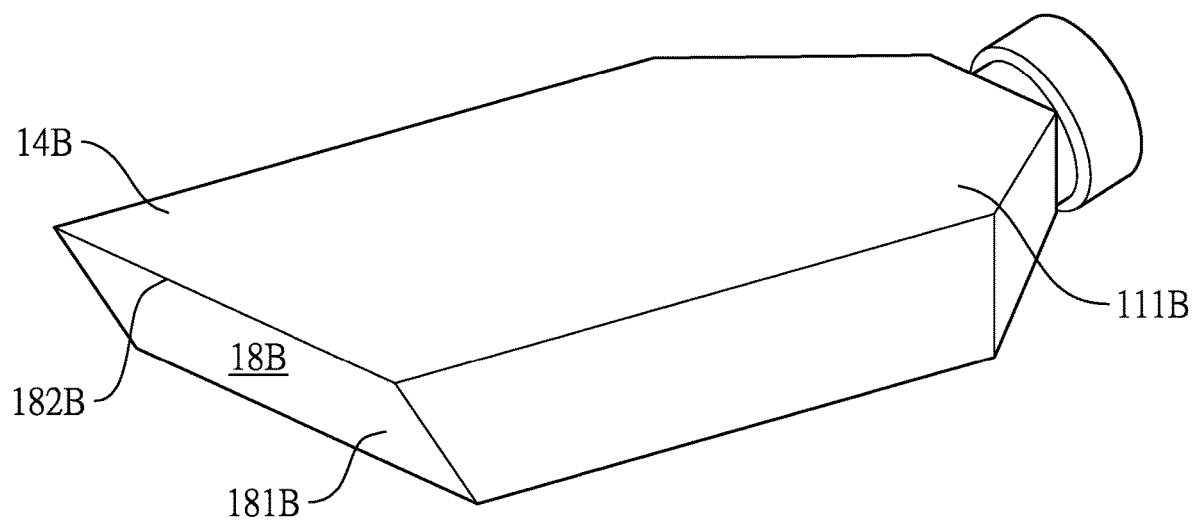
FIG. 3 is a perspective view of a third embodiment of a culture flask in accordance with the present invention.

With reference to FIG. 3, a third embodiment in accordance with the present invention is substantially similar to the second embodiment mentioned above, but the difference is that the bottom 182B of the collecting recess 18B is one edge of the upper translucent plane 111B. Part of the upper translucent plane 111B which is closer to the recess end 14B forms one lateral face of the annular wall 181B of the collecting recess 18B.

With reference to FIG. 4, a fourth embodiment in accordance with the present invention is substantially similar to the second embodiment mentioned above, but the difference is that the bottom 182C of the collecting recess 18C is a straight line that is perpendicular to and connects the upper translucent plane 111C and the lower translucent plane 112C, and therefore the shape of a lateral face of the collecting recess 18C connected to the upper translucent plane 111C is an isosceles triangle. The base of said isosceles triangle is connected to the upper translucent plane 111C.

With reference to FIG. 5, a fifth embodiment in accordance with the present invention is substantially similar to the third embodiment mentioned above, but the difference is that the position of the flask opening 13D is closer to the upper translucent plane 111D than it is to the lower translucent plane 112D. The bottom 182D of the collecting recess 18D is one edge of the upper translucent plane 111D. Part of the upper translucent plane 111D which is closer to the recess end 14D forms one lateral face of the annular wall 181D.

With reference to FIG. 6, a sixth embodiment in accordance with the present invention is substantially similar to the first embodiment mentioned above, but the difference is that the flask opening 13E is closer to the upper translucent plane 111E than it is to the lower translucent plane 112E.

With reference to FIG. 7, a seventh embodiment in accordance with the present invention is substantially similar to the fifth embodiment mentioned above, but the difference is that the bottom 182F of the collecting recess 18F is one edge of the lower translucent plane 112F. Part of the lower translucent plane 112F which is closer to the recess end 14F forms one lateral face of the annular wall 181F.

With reference to FIG. 8, an eighth embodiment in accordance with the present invention is substantially similar to the fourth embodiment mentioned above, but the difference is that the position of the flask opening 13G is closer to the upper translucent plane 111G than it is to the lower translucent plane 112G.

With reference to FIG. 9, a ninth embodiment in accordance with the present invention is substantially similar to the first embodiment mentioned above, but the shape of the collecting recess 18H is different.

In a preferred embodiment, the collecting recess 18H further comprises an annular wall 181H and an end segment 183H. Said annular wall 181H is connected to said end segment 183H. The cells with a total volume far less than the culture medium can therefore be collected inside the end segment 183H, but the shape of the collecting recess 18H is not limited by the abovementioned. In a preferred embodiment, there can be no end segment 183H. In a preferred embodiment, a shape of the annular wall 181H is in the shape of a dome, and the end segment 183H is a curved surface protruding outward, but the shape of the annular wall 181H is not limited by the abovementioned. For example, the shape of annular wall 181H can be a pyramid, as long as the cells can slip along an inner surface of the annular wall 181H toward the end segment 183H and finally being collected inside the end segment 183H.

Figure 10:
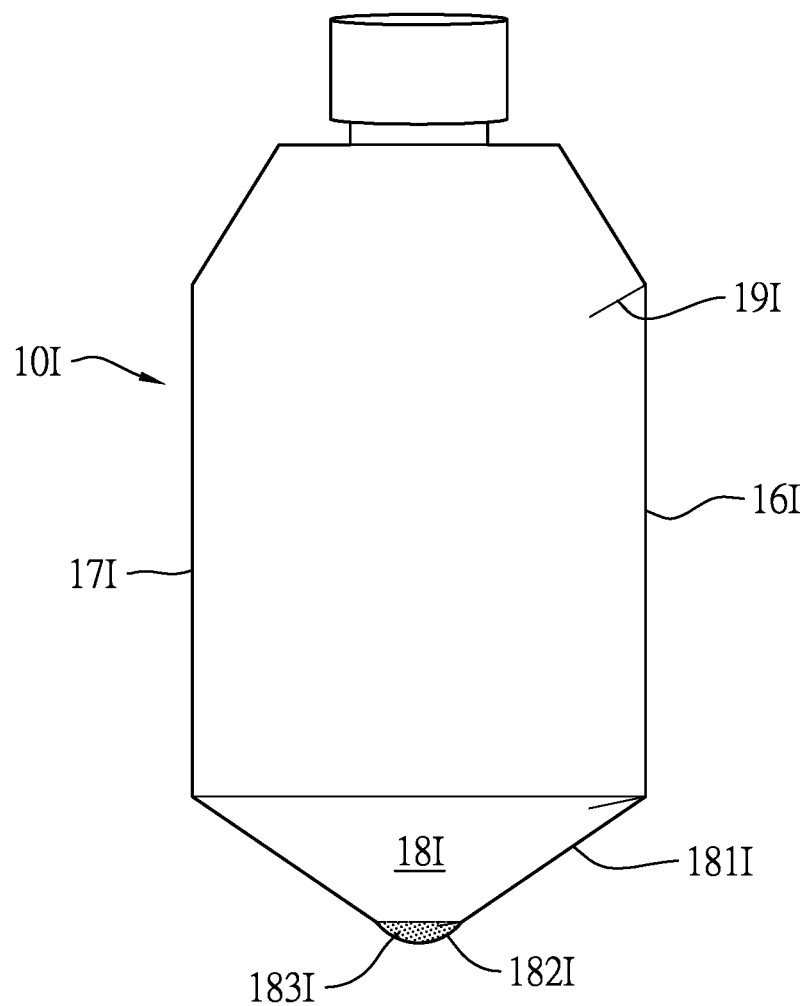
FIG. 10 is a top view of a tenth embodiment of a culture flask in accordance with the present invention.
Figure 11:
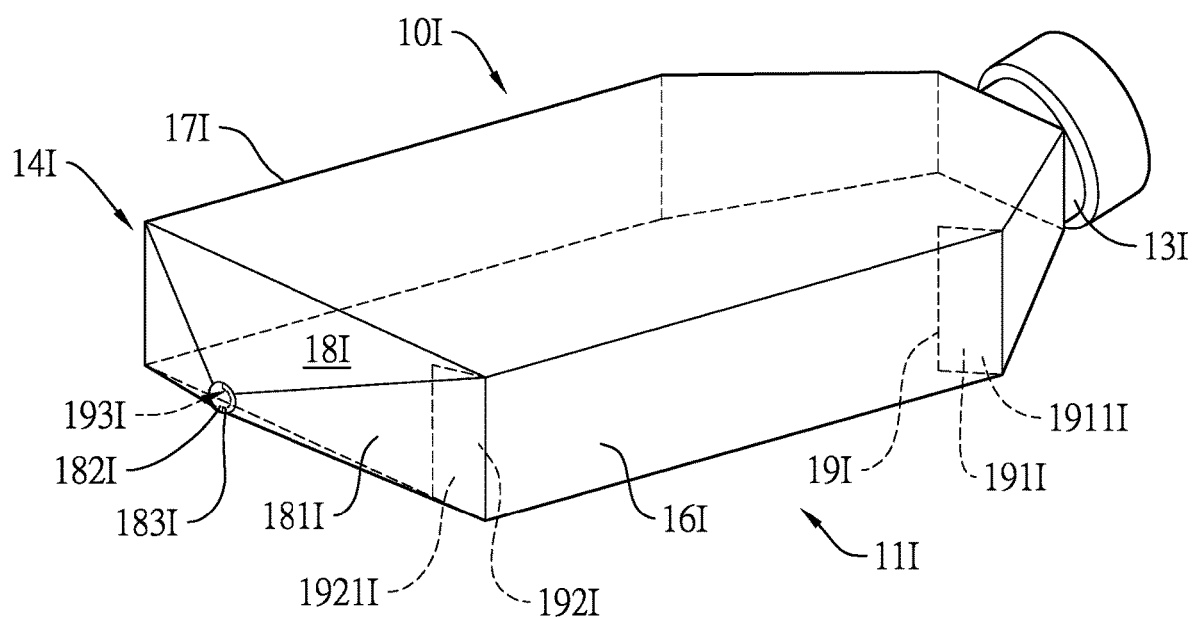
FIG. 11 is a perspective view of the culture flask in FIG. 10.

With reference to FIGS. 10 and 11, a tenth embodiment in accordance with the present invention is substantially similar to the ninth embodiment mentioned above, but the shape of the annular wall 181I of the collecting recess 18I and the configuration of the flask body 10I are different. In a preferred embodiment, the shape of the annular wall 181I of the collecting recess 18I is a pyramid. The end segment 183I is still a curved surface protruding outward, that is, the bottom 182I of the collecting recess 18I is dome shaped. Two plate-shaped blockers 19I are formed on the inner surface of the flask body 10I, but the number of blockers 19I is not limited to two. For example, there can be only one blocker 19I formed inside the flask body 10I, or there can be no blocker 19I formed on the flask body 10I at all. In addition, the shape of the blocker 19I is not limited to that of a plate, as long as the blocker is formed on the inner surface of the flask body 10I and can stop the cells from slipping freely inside the inner surface of the flask body 10I. For example the blocker 19I can be formed by making a dent on the outer face of the front side 16I, and resulting in a protrusion on the inner face of the front side 16I which forms the blocker.

In a preferred embodiment, the blockers 19I are formed on an inner surface of the flask body excluding the two translucent planes 11I, and the blockers 19I extend toward the two translucent planes 11I until two sides of the blocker 19I are connected to the two translucent planes 11I respectively. The blocker 19I, the inner surface of the flask body 10I, and the two translucent planes 11I form a gathering recess. To be precise, the blockers 19I are formed both on the front side 16I and on the annular wall 181I of the collecting recess 18I. When the user observes the cells through the translucent planes 11I, minimum area on the translucent planes 11I is hindered by the blockers 19I because the direction in which the blockers 19I extend is the same as the direction of observation. However, the position of the blockers 19I is not limited by the abovementioned.

In a preferred embodiment, the blockers 19I are formed on an inner surface of the flask body excluding the two transparent planes 11I, and the blockers 19I extend toward the two transparent planes 11I until two sides of the blocker 19I are connected to the two transparent planes 11I respectively. The blocker 19I, the inner surface of the flask body 10I, and the two transparent planes 11I form a gathering recess. To be precise, the blockers 19I are formed both on the front side 16I and on the annular wall 181I of the collecting recess 18I. When the user observes the cells through the translucent planes 11I, miniumum area on the translucent planes 11I is hindered by the blockers 19I because the direction in which the blockers 19I extend is the same as the direction of observation. However, the position of the blockers 19I is not limited by the abovementioned.

In a preferred embodiment, the blockers 19I include a first blocker 191I and a second blocker 192I. The first blocker 191I and the second blocker 192I are formed on the inner surface of the flask body 10I, but the number of the blockers 19I formed on the inner surface of the flask body 10I is not limited by the abovementioned. For example, there can be only one blocker 19I formed on the inner face of the flask body 10I. In a preferred embodiment, the first blocker 191I and the second blocker 192I have a first blocking surface 1911I and a second blocking surface 1921I, respectively. The blocking surface 1911I and blocking surface 1921I face toward the recess end 14I and both said blocking surfaces incline towards the recess end 14I. Due to said inclination of the blocking surfaces 1911I and 1921I, cells are blocked and trapped by an angled area formed between said blocking surfaces 1911I and 1921I and the inner face of the front side 16I when the user empties culture medium inside the flask body 10I by tilting. More cells can be preserved inside the flask body 10I after replacement of the culture medium by blocking and trapping cells that detach from the surface of the flask body 10I. However, the inclination of the blocking faces of the blockers 19I is not limited to a direction toward the recess end 14I.

In a preferred embodiment, a blocking panel 193I is formed in the collecting recess 18I and located next to the bottom 182I of the collecting recess 18I.

In a preferred embodiment, the bottom 182I of the collecting recess 18I is dome shaped; the blocking panel 193I located next to the bottom 182I of the collecting recess 18I extends along the bottom 182I of the collecting recess 18I and the blocking panel 193I is in the shape of an arc. However, the shape of the blocking panel 193I is not limited by the abovementioned. The blocking panel 193I can be in other shapes as long as said shape corresponds to the inner shape of the bottom 182I, and the blocking panel 193I is formed in the collecting recess 18I and located next to the bottom 182I. For example, when the shape of a collecting recess is a pyramid with a rectangular bottom, the shape of the blocking panel is a trapezoid formed in the collecting recess 18I.

Figure 12:
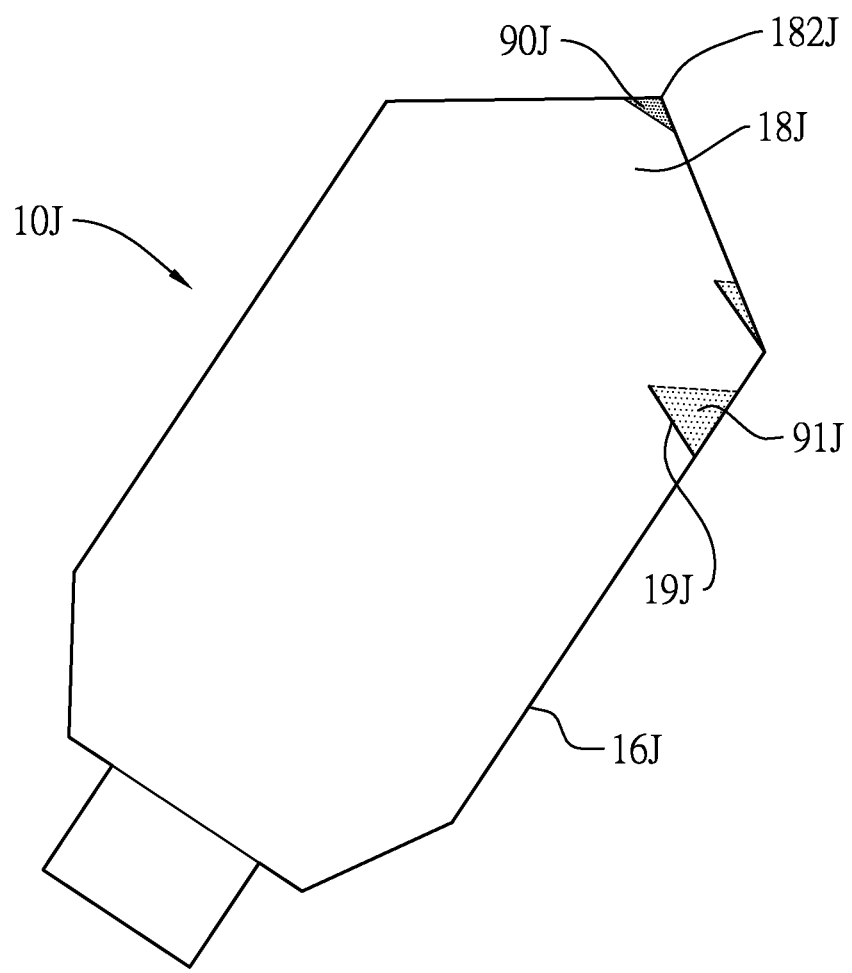
FIG. 12 is a side view of an eleventh embodiment of a culture flask in accordance with the present invention, shown tilted.

With reference to FIG. 12, an eleventh embodiment in accordance with the present invention is substantially similar to the tenth embodiment mentioned above, but the number of the blocker 19J is two, and both blockers 19J are formed on the front side 16J. No blocker 19J is formed in the collecting recess 18J.

Figure 13:
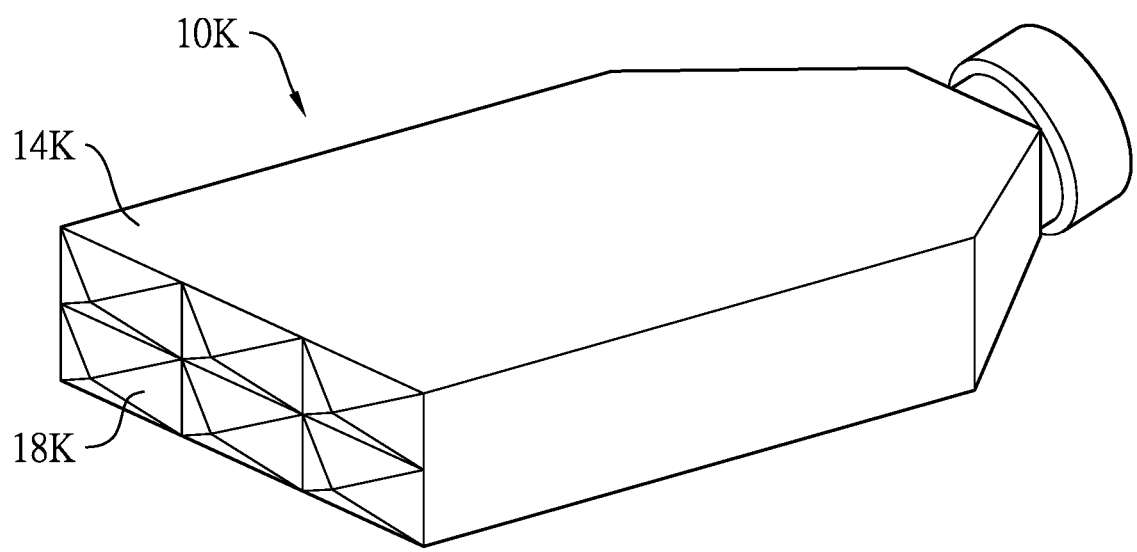
FIG. 13 is a perspective view of a twelfth embodiment of a culture flask in accordance with the present invention.

With reference to FIG. 13, a twelfth embodiment in accordance with the present invention is substantially similar to the first embodiment mentioned above, but the number of the collecting recesses 18K is six. To be precise, the six collecting recesses 18K on the recess end 14K are arranged in an array and are closely packed and occupy the whole surface area of the recess end 14K of the flask body 10K.

Figure 14:
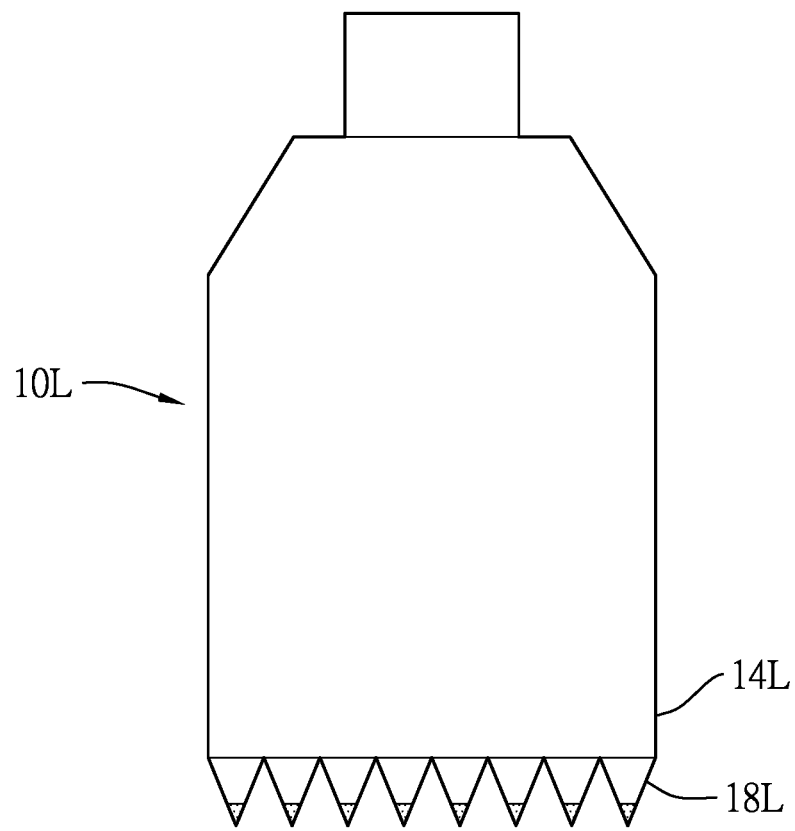
FIG. 14 is a top view of a thirteenth embodiment of a culture flask in accordance with the present invention.
Figure 15:
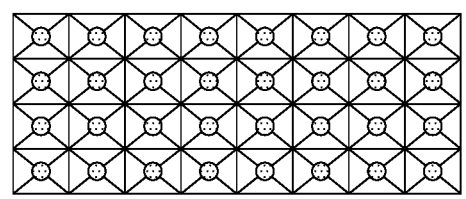
FIG. 15 is a left view of the culture flask in FIG. 14.

With reference to FIGS. 14 and 15, a thirteenth embodiment in accordance with the present invention is substantially similar to the twelfth embodiment mentioned above, but the number of the collecting recess 18L is thirty-two.

Figure 16:
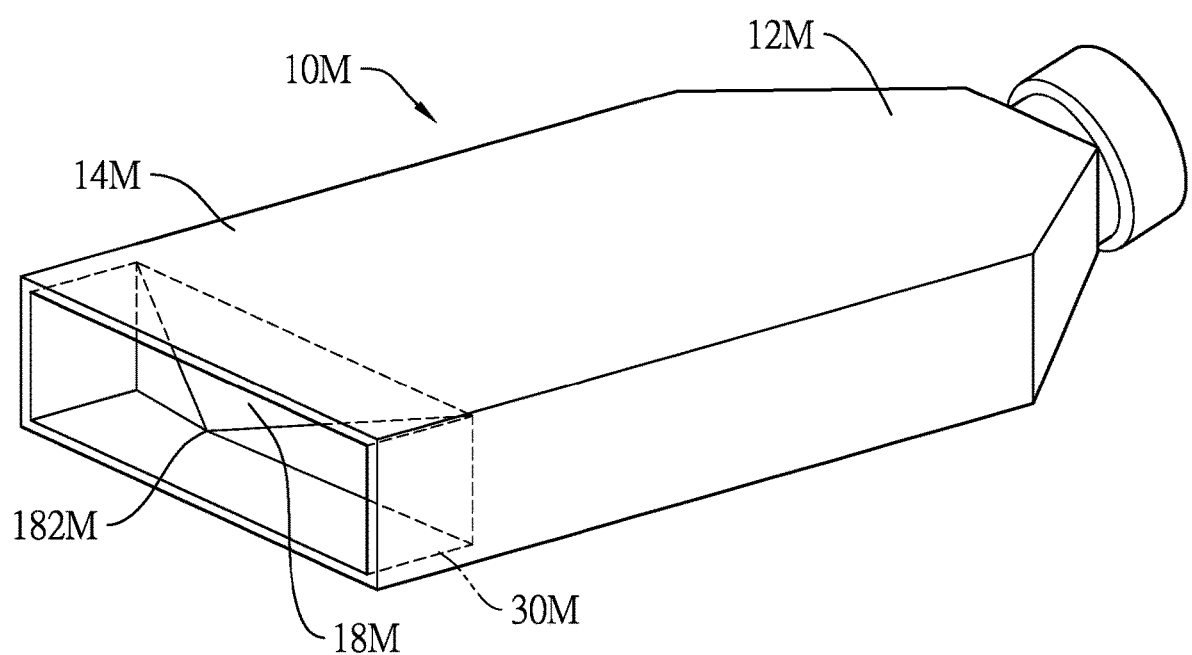
FIG. 16 is a perspective view of a fourteenth embodiment of a culture flask in accordance with the present invention.

With reference to FIG. 16, a fourteenth embodiment in accordance with the present invention is substantially similar to the first embodiment mentioned above, but the culture flask further comprises a flask stand 30M. The flask stand 30M is connected to the recess end 14M of the flask body 10M. The flask stand 30M extends further than the bottom 182M of the collecting recess 18M in a direction away from the opening end 12M. To be precise, the flask stand 30M is an annular wall surrounding the recess end 14M of the flask body 10M, but the shape of the flask stand 30M is not limited to an annular wall. For example, the flask stand 30M can be a plurality of columns, as long as the flask stand can keep the culture flask in an upright position with the recess end 14M facing downward. All the abovementioned embodiments can further comprise a flask stand in order to be kept at an upright position.

Figure 17:
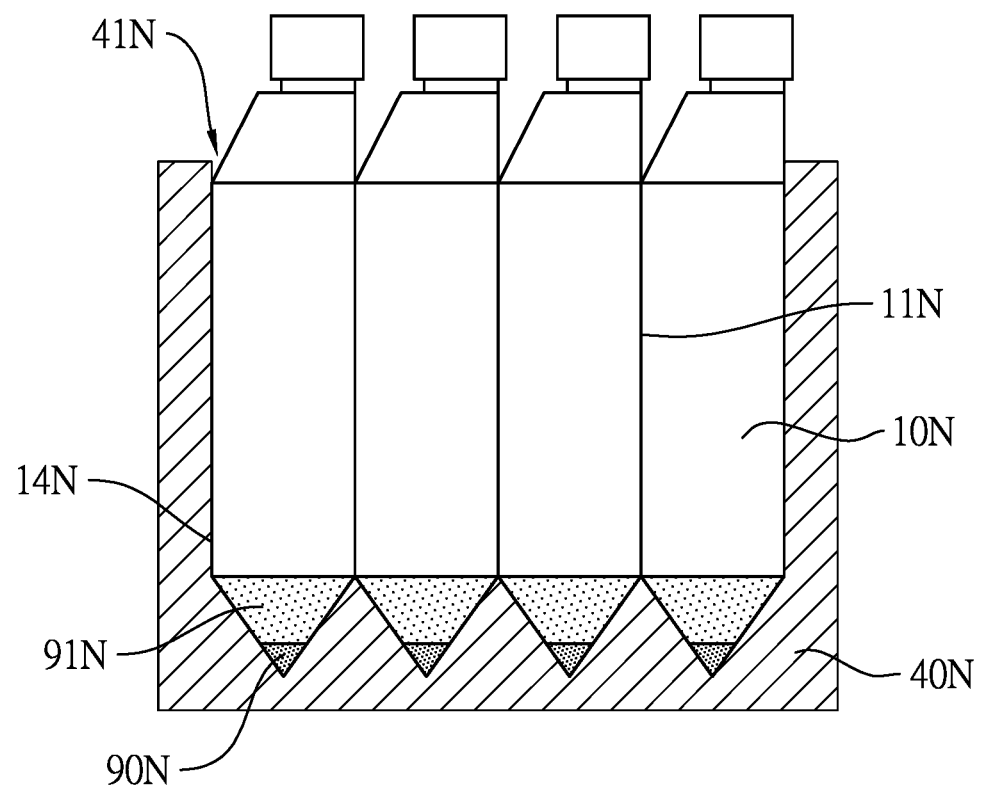
FIG. 17 is a side view of a culture flask assembly in accordance with the present invention.

With reference to FIG. 17, a first embodiment of a culture flask assembly in accordance with the present invention comprises four culture flasks and an adapter 40N. The culture flasks are in accordance with the sixth embodiment of culture flask. In a preferred embodiment, the number of the culture flask is four, but there can be only one culture flask in the culture flask assembly. At least one bucket 41N is formed on the top the adapter 40N. The shape of the bucket 41N corresponds to the shape of the flask body 10N.

In a preferred embodiment, the shape of the bucket 41N corresponds to the shape of four identical culture flasks leaning against each other by the translucent plane 11N. The number of the bucket 41N is not limited to one, and the shape of the bucket 41N is not limited by the abovementioned, as long as all culture flasks of the culture flask assembly can be mounted into the adapter, and meanwhile the shapes of all the culture flasks corresponds to all the buckets. For example, the adapter 40N can have four separate buckets 41N not connected to each other.

With reference to FIG. 1, to use the present invention, first put the culture medium and the cells inside the flask body 10 of the culture flask, and then fasten the flask cap 20 onto the flask opening 13 by threading. Lay flat the flask body 10 with the lower translucent plane 112 facing downward and being horizontal. User can observe the culturing progress inside the culture flask using optical instrument through the translucent plane 11.

With reference to FIG. 17, when the composition of culture medium changes due to metabolism of the cells, insert the culture flasks 14N into the adapter 40N, and then insert the adapter 40N with the culture flask 14N into the centrifuge for separation. However, the abovementioned procedure is no limited, as long as the shape of the culture flask can be corresponding to the holes inside the centrifuge, and therefore the culture flask can be inserted directly into the centrifuge without using an adapter. After centrifugation, the culture cells sediment to the bottom of the culture flask while the used culture medium 91N stays on top of the sediment cells 90N. User can now remove the used culture medium 91N using a suction tube.

With reference to FIG. 12, when a culture flask has blockers 19J, user can remove the used culture medium 91J on top of the cells by tilting the flask body 10J. The blockers 19J prevent sediment cells 90J from leaving the culture flask even if the sediment cells 90J are washed by the culture medium and detach from the inner surface of the flask body. After removing the used culture medium 91J, user puts fresh culture medium into the flask body. The culture flask is then shaken in order for cells to distribute evenly inside the culture medium, and then the culture flask is restored to the horizontal position with the lower translucent plane 112 facing downward.

With reference to FIGS. 14 and 15, when the culture flask has multiple collecting recesses 18L arranged in an array, cells are evenly distributed inside each collecting recess 18L after centrifugation. Therefore, after adding fresh culture medium, user can continue cell culturing with the recess end 14L facing downward. In this case the cells can be evenly distributed inside each collecting recess 18L in the recess end 14L, and continue culturing with 3D structure, or conducting cellular differentiation experiments with 3D structure.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A culture flask, configured to contain a culture medium and adapted for centrifugation; the culture flask comprising:
   a flat flask body having two translucent planes forming two major flat surfaces located on two opposite sides of the flask body respectively, and the two translucent planes being parallel to each other; at least one of the translucent planes being transparent;

two side surfaces located between the two major flat surfaces and connecting the two major flat surfaces, each side surface having an area smaller than an area of each of the two major flat surfaces;

an opening end located on one end of the flask body, and a flask opening formed on the opening end, and the flask opening communicating with an inner space of the flask body;

a recess end located opposite to the opening end on the flask body; an imaginary straight line passing through both the opening end and the recess end being defined as a centrifuging line; and at least one collecting recess configured to collect cells in the culture medium; the at least one collecting recess formed on the recess end and extending from distal ends of the two major flat surfaces and two side surfaces, along the centrifuging line in a direction away from the opening end, and an area of a cross section of the at least one collecting recess that is perpendicular to the centrifuging line being gradually decreased toward a bottom of the at least one collecting recess along said direction such that the cells are collected inside the bottom of the at least one collecting recess after centrifugation; and at least one blocker protruding from an inner surface of one of the two side surfaces of the flask body and extending between the two translucent planes with two sides of the at least one blocker connected to the two translucent planes respectively;

wherein the at least one blocker, the inner surface of said one of the two side surfaces of the flask body, and the two translucent planes form at least one gathering recess; the at least one blocker has a blocking surface toward the recess end, and the blocking surface inclines toward the recess end with respect to a plane perpendicular to the two translucent planes, such that an opening of the gathering recess faces toward the recess end to trap and preserve cells moving from the recess end toward the flask opening when a user removes the culture medium by tilting.

2. The culture flask as claimed in claim 1, wherein the at least one collecting recess is an elongated slot.

3. The culture flask as claimed in claim 1, wherein the at least one collecting recess is in the shape of a pyramid.

4. The culture flask as claimed in claim 1, wherein the at least one collecting recess comprises
an annular wall in the shape of a pyramid; and
an end segment connected to the annular wall and being a curved surface protruding outward.

5. The culture flask as claimed in claim 1, wherein the at least one collecting recess comprises
an annular wall in the shape of a dome; and
an end segment connected to the annular wall and being a curved surface protruding outward.

6. The culture flask as claimed in claim 1, wherein the culture flask further comprises a flask stand connected to the recess end of the flask body; the flask stand extends further than the bottom of the collecting recess in a direction away from the opening end.

7. A culture flask assembly comprising:
at least one said culture flask as claimed in claim 1; and
an adapter having at least one bucket formed on a top of the adapter; a shape of the at least one bucket corresponding to a shape of the at least one culture flask; the at least one culture flask being able to be inserted into the adapter.

* * * * *